US011224572B1

(12) United States Patent
Shanmugam et al.

(10) Patent No.: US 11,224,572 B1
(45) Date of Patent: Jan. 18, 2022

(54) STABLE ORAL LIQUID COMPOSITION OF TERAZOSIN

(71) Applicant: Novitium Pharma LLC, East Windsor, NJ (US)

(72) Inventors: Muthusamy Shanmugam, East Windsor, NJ (US); Palanisamy Sivakumar, Tamil Nadu (IN)

(73) Assignee: Novitium Pharma LLC, East Windsor, NJ (US)

( * ) Notice: Subject to any disclaimer, the term of this patent is extended or adjusted under 35 U.S.C. 154(b) by 0 days.

(21) Appl. No.: 17/163,848

(22) Filed: Feb. 1, 2021

(30) Foreign Application Priority Data

Aug. 17, 2020 (IN) .............................. 202041035308

(51) Int. Cl.

| | | |
|---|---|---|
| *A61K 31/135* | (2006.01) | |
| *A61K 31/505* | (2006.01) | |
| *A61K 9/08* | (2006.01) | |
| *A61K 47/10* | (2017.01) | |
| *A61K 9/00* | (2006.01) | |
| *A61K 31/517* | (2006.01) | |
| *A61K 47/26* | (2006.01) | |

(52) U.S. Cl.
CPC .............. *A61K 9/08* (2013.01); *A61K 9/0053* (2013.01); *A61K 31/517* (2013.01); *A61K 47/10* (2013.01); *A61K 47/26* (2013.01)

(58) Field of Classification Search
CPC ....................................................... A61K 9/08
See application file for complete search history.

(56) References Cited

U.S. PATENT DOCUMENTS

| | | |
|---|---|---|
| 4,026,894 A | 5/1977 | Winn et al. |
| 4,251,532 A | 2/1981 | Roteman |
| 5,212,176 A * | 5/1993 | Kyncl ................. C07D 405/12 514/252.17 |
| 5,294,615 A | 3/1994 | Meyer et al. |
| 5,587,377 A | 12/1996 | Patel et al. |
| 6,110,493 A | 8/2000 | Guentensberger et al. |
| 2018/0098978 A1* | 4/2018 | Brauer ...................... A61P 9/12 |

FOREIGN PATENT DOCUMENTS

| | | | |
|---|---|---|---|
| WO | WO2010065492 | * | 12/2009 |
| WO | 2016197738 A1 | | 12/2016 |
| WO | WO2016197738 | * | 12/2016 |

OTHER PUBLICATIONS

Liu et al. (Efficacy of Combined Amlodipine/Terazosin Therapy in male Hypertensive Patients with Lower Urinary Tract Symptoms: a Randomized, Double-Blink Clinical Trial) (Year: 2009).*
G. L. Flynn, "Buffers—pH Control within Pharmaceutical Systems," J. Parenteral Drug Assoc. (1980) 34(2): 139-162.
HYTRIN® (terazosin hydrochloride) tablet prescribing information as of Jul. 10, 2009 (27 pgs.).
Mafco Worldwide LLC entitled "Magnasweet® INNOVATES" (Aug. 2018); 4 pages.
Ternay, A.L., Contemporary Organic Chemistry, Second Edition (1979), pp. 101-102.
Chemical Abstracts Registry No. 60548-08-5 related to Terazosin Related Compound A (2021); 1 page.
USP Certificate for Terazosin Related Compound A (2017); 1 page.

* cited by examiner

*Primary Examiner* — Sarah Alawadi

(74) *Attorney, Agent, or Firm* — Daniel R. Evans; Merchant & Gould P.C.

(57) ABSTRACT

The present invention relates to novel stable oral liquid composition of Terazosin and its pharmaceutically acceptable salt which is useful for treating symptomatic benign prostatic hyperplasia (BPH) and hypertension.

20 Claims, No Drawings

STABLE ORAL LIQUID COMPOSITION OF TERAZOSIN

RELATED APPLICATION

The present application claims priority to Indian Patent Application No. 202041035308, filed on Aug. 17, 2020, is incorporated by reference in its entirety.

FIELD OF THE INVENTION

The disclosure relates to a stable oral liquid composition comprising terazosin or a pharmaceutically acceptable salt thereof, which is useful for treating symptomatic benign prostatic hyperplasia (BPH) and hypertension.

BACKGROUND OF THE INVENTION

Terazosin hydrochloride is chemically known as (RS)-Piperazine, 1-(4-amino-6, 7-dimethoxy-2-quinazolinyl)-4-[(tetrahydro-2-furanyl)carbonyl]-, monohydrochloride.

Terazosin hydrochloride, an alpha-1-selective adrenoceptor blocking agent, is a quinazoline derivative used for the treatment of symptomatic benign prostatic hyperplasia (BPH). There is a rapid response, with approximately 70% of patients experiencing an increase in urinary flow and improvement in symptoms of BPH when treated with terazosin. The long-term effects of terazosin on the incidence of surgery, acute urinary obstruction or other complications of BPH are yet to be determined. The development of symptomatic BPH is considered to be an inescapable phenomenon for the aging male population. Symptomatic BPH is observed in approximately 70% of males over the age of 70. A medicinal alternative to surgery is clearly very desirable. The limitations of surgery for treating symptomatic BPH include the morbidity rate of an operative procedure in elderly men, persistence or recurrence of obstructive and irritative symptoms, as well as the significant cost of surgery.

Terazosin hydrochloride is also indicated for the treatment of hypertension. Terazosin hydrochloride can be used alone or in combination with other antihypertensive agents such as diuretics or beta adrenergic blocking agents. Terazosin hydrochloride, including its hydrated forms, is an α1-adrenoceptor blocker, which optionally acts on α1-adrenoceptor and reduces high blood pressure down with the resistance that reduces peripheral vessels, so it can significantly reduce the blood pressure with hypertensive hyperplasia of prostate patient.

In animals, terazosin causes a decrease in blood pressure by decreasing total peripheral vascular resistance. The vasodilatory hypotensive action of terazosin appears to be produced mainly by blockade of alpha-1 adrenoceptor. Terazosin decreases blood pressure gradually within 15 minutes following oral administration. Patients in clinical trials of terazosin were administered once daily (the great majority) and twice daily regimens with total doses usually in the range of 5 to 20 mg/day, and had mild (about 77%, diastolic pressure 95 to 105 mmHg) or moderate (23%, diastolic pressure 105 to 115 mmHg) hypertension. Because terazosin, like all alpha antagonists, can cause unusually large drops in blood pressure after the first dose or first few doses, the initial dose was 1 mg in virtually all trials, with subsequent titration to a specified fixed dose or titration to some specified blood pressure end point (usually a supine diastolic pressure of 90 mmHg). Accordingly, the HYTRIN® prescribing information recommends an initial terazosin dose of 1 mg for both symptomatic BPH and hypertension, with subsequent dose modifications up to 10-20 mg.

Commercially available terazosin hydrochloride (e.g., HYTRIN®) is a tablet and capsule. The tablet/capsule forms of terazosin hydrochloride have long disintegration time, and thus, dissolution and dissolution rate are lower. The disintegration/dissolution properties of this dosage form results in absorption variability and low bioavailability. The commercially available dosage forms of terazosin hydrochloride (viz., tablets and capsules) may lead a decrease in patient compliance, especially for patients that are elderly, bed-ridden, and/or dysphagic.

U.S. Pat. No. 4,026,894 relates generally to terazosin and its hydrochloride salt. This patent identifies various formulations for treating hypertension by administering terazosin and its hydrochloride salt by intraperitoneal, oral and intravenous routes. This patent identifies the various dosage forms such as tablets, capsules and pills for oral administration and solution and suspension for parenteral administration. This patent is silent about specific excipients for oral preparations and stability of dosage forms.

U.S. Pat. No. 4,251,532 relates generally to a crystalline dihydrate form of terazosin hydrochloride.

U.S. Pat. No. 5,212,176 relates generally to an enantiomeric form of terazosin, viz., R-(+)-terazosin and its pharmaceutically acceptable salts. This patent generally identifies various dosage forms including solid dosage forms such as tablets, dragees, capsules, pills, and granules, liquid dosage forms for oral administration include pharmaceutically acceptable emulsions, solutions, suspensions, syrups and elixirs and compositions for rectal or vaginal administration are preferably suppositories. The patent does not disclose any particularly exemplified dosage forms or the preparation thereof.

Unless particular dosage forms are made, one cannot predict the degradation and stability of that particular dosage particularly liquid dosage because its stability depends on multiple factors such as pH, buffers, preservatives, vehicles, etc. It is well known fact that the enantiomer and racemic compounds have different physico-chemical properties and bioavailability. Thus, one cannot expect the same activity for an enantiomeric form when compared to its racemic form. For instance, the enantiomeric form (compared to the racemate): (i) may be more active or more toxic, (ii) may be more stable or less stable, (iii) may degrade when formulated, (iv) may result in an adverse effect during administration, and (v) may have a different distribution and release profile in animals. Accordingly, the generalized statement for the preparation of dosage is not useful for the preparation of dosage forms in any drugs.

U.S. Pat. No. 5,294,615 relates generally to a crystalline polymorph of terazosin hydrochloride and a dosage form such as soft gelatin capsule containing terazosin hydrochloride in a non-aqueous liquid carrier and indicates that polyethylene glycol is a preferred non-aqueous liquid carrier. The soft gelatin capsule formulation containing the active ingredient suspended in a non-aqueous liquid carrier composed primarily of polyethylene glycol with some glycerin present. The main drawback of this dosage form is the stability of this dosage form is unknown.

U.S. Pat. No. 6,110,493 relates generally to a capsule dosage form, process for preparation and its stability data of this dosage form.

U.S. Pat. No. 5,587,377 relates generally to terazosin hydrochloride monohydrate polymorph IV and it is used for the preparation of tablet dosage forms.

There are many routes of treatment available for drug administration. Based on simplicity, oral administration of drugs is one of the preferred routes for treatment. As stated above, terazosin hydrochloride is also administered by oral in the form of tablet and capsule for treating symptomatic BPH and hypertension. It is generally known that certain segments of the population have difficulty ingesting and swallowing solid oral dosage forms such as tablets and capsules particularly children, geriatric population, and hospitalised patients. Further, solid dosage forms are not recommended for children or elderly due to increased risk in choking.

Additionally, certain solid oral dosage forms of medications cannot be administered simply by crushing (e.g., patients requiring various types of feeding tubes) because of the coating or drug delivery mechanism. Many people in the total population have this difficulty which leads to non-compliance with the recommended medical therapy with the solid dosage forms, thereby resulting in rendering the therapy ineffective.

Additionally, the dose of terazosin to be given to paediatric, geriatric, and patients with feeding tubes are calculated according to the patient's weight. When the calculated dose is something other than the amount present in one or more intact solid dosage forms, the solid dosage form must be divided to provide the correct dose. This leads to the likelihood of inaccurate dosing when solid dosages forms, such as tablets and capsules are compounded to prepare other formulations for the aforementioned patients.

Otherwise the compounding pharmacist break and crush the terazosin hydrochloride tablets or capsule into a powder via mortar and pestle and reconstitute the powder in some liquid form. It is another method to overcoming the use of the tablet and capsule form to children, the geriatric, and patients with feeding tubes. This method has significant drawbacks of including large variability in the actual dosage, rapid instability, and inconsistent formulation methods per compounding pharmacy, incomplete solubilizing of the terazosin tablet or capsule in the liquid and a number of other potential issues. The liquid formulation obtained by crushing tablet or capsule may also be potentially unsafe due to contamination with residual drugs and other substances from the mortar and pestle or other crushing agent.

In view of the foregoing, there is a need for a safe, pharmaceutically elegant, and stable terazosin liquid composition which may be adapted for administration to certain patient populations that overcome the drawbacks with solid pharmaceutical compositions.

The inventors surprisingly discovered a liquid composition for oral administration comprising terazosin or a pharmaceutically acceptable salt thereof, which exhibits long-term stability with respect to terazosin content. The liquid composition disclosed herein is safe and available for oral administration especially for geriatric population and hospitalized patients. The liquid composition disclosed herein provides a better solution for above said problems.

OBJECTIVE OF THE INVENTION

An objective disclosed herein relates to a pharmaceutically acceptable liquid formulation for oral administration comprising terazosin or a pharmaceutically acceptable salt thereof.

SUMMARY OF THE INVENTION

Disclosed herein is a liquid composition for oral administration, comprising:
i. about 0.5 to about 5 mg/mL of terazosin or a pharmaceutically acceptable salt thereof;
ii. at least one pH modifier; and
iii. at least one pharmaceutically acceptable excipient;
wherein the pH of the liquid composition ranges from about 4.5 to about 6.5.

DETAILED DESCRIPTION OF THE INVENTION

The following paragraphs detail various embodiments of the invention. For the avoidance of doubt, it is specifically intended that any particular feature(s) described individually in any one of these paragraphs (or part thereof) may be combined with one or more other features described in one or more of the remaining paragraphs (or part thereof). In other words, it is explicitly intended that the features described below individually in each paragraph (or part thereof) represent important aspects of the invention that may be taken in isolation and also combined with other important aspects of the invention described elsewhere within this specification as a whole, and including the examples and figures. The skilled person will appreciate that the invention extends to such combinations of features and that these have not been recited in detail here in the interests of brevity.

Definitions of some of the terms used herein are detailed below.

The use of the terms "a" and "an" and "the" and similar references in the context of describing the liquid composition described herein (especially in the context of the following claims) are to be construed to cover both the singular and the plural, unless otherwise indicated herein or clearly contradicted by context.

The term "about" as used herein embodies standard error associated with a physico-chemical observable. As used herein, the term "about" means a slight variation of the value specified, for example, within 10% of the value specified. A stated amount for a compositional ingredient that is not preceded by the term "about" does not mean that there is no variance for the stated term, as one of ordinary skill would understand that there may be the possibility of a degree of variability generally associated with experimental error.

The term "therapeutically effective amount" or effective dose" as used herein refers to the amount or dose of terazosin that is sufficient to initiate therapeutic response in a patient.

One embodiment relates to a liquid composition for oral administration, comprising: (i) about 0.5 to about 5 mg/mL of terazosin or a pharmaceutically acceptable salt thereof; (ii) at least one pH modifier; and (iii) at least one pharmaceutically acceptable excipient; wherein the pH of oral liquid composition is about 4.5 to 6.5.

In one embodiment, the liquid composition comprises terazosin hydrochloride.

In another embodiment, the liquid composition comprises terazosin hydrochloride in an amount of about 0.5 mg/mL to 5 mg/mL based on terazosin.

In another embodiment, the liquid composition comprises terazosin hydrochloride in an amount of about 1 mg/mL to 4 mg/mL based on terazosin.

In another embodiment, the liquid composition comprises terazosin hydrochloride in an amount of about 1 mg/mL based on terazosin.

In yet another embodiment, the at least one pH modifier is selected from group consisting of citric acid, malic acid, hydrochloric acid, phosphoric acid, ammonium chloride, potassium bicarbonate, potassium carbonate, sodium acetate, sodium chloride, trisodium citrate salts, sodium hydroxide, sodium phosphate, sodium thiosulfate, tartaric acid, calcium chloride, sodium bisulphate, fumaric acid, sodium dihydrogen phosphate monohydrate, disodium hydrogen phosphate dihydrate and potassium phosphate, and a combination thereof.

In another embodiment, the at least one pH modifier is a combination of aforementioned pH modifiers and when combinations are used it also acts as buffer. When a buffer is present, it serves to maintain the pH of the liquid compositions disclosed herein within a defined range. Suitable buffers include those buffers described in, for example, G. L. Flynn, "Buffers—pH Control within Pharmaceutical Systems," J. Parenteral Drug Assoc. (1980) 34(2): 139-162. A suitable buffer is one that is not only capable of maintaining a pH that ranges from 4.5 to 6.5, but also be compatible with the stable oral liquid compositions disclosed herein. Suitable contemplated buffers include, for example, one or more of citrate, acetate, aconitate, glutarate, glutamate, malate, succinate, tartrate, and phosphate. A specifically contemplated buffer is comprised of citric acid, monobasic citrate, dibasic citrate, and tribasic citrate, in which the mono-, di-, or tribasic citrate forms have associated counterions and thus, may collectively be referred to as citrate salts, or in particular, a citrate salt. The associated counterions include, for example, sodium, potassium, ammonium, calcium, etc. For instance, a particular citrate salt contemplated herein is sodium citrate, which may exist as a hydrated form, such as, a dihydrate or a pentahydrate. One of ordinary skill will understand that the molar amounts of citric acid and sodium citrate, relative to each other, will depend on the pH of the composition. Therefore, one of ordinary skill would appreciate that the amount of citrate (i.e., citric acid and sodium citrate) in the liquid composition refers to the amount added during manufacture. In a particular embodiment, the pH of the liquid composition ranges from about 4.5 to about 6.5.

In an embodiment of the liquid composition disclosed herein, the amount of pH modifier ranges from about 0.05 mg/ml to about 2 mg/ml. In some embodiments the liquid composition comprises about 0.05 mg/ml, about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1.0 mg/mL, about 1.2 mg/mL, about 1.4 mg/mL, about 1.6 mg/mL, about 1.8 mg/mL or about 2.0 mg/mL.

In an embodiment of the liquid composition disclosed herein, the at least one pharmaceutically acceptable excipient comprises a vehicle, a preservative, a sweetener, or a combination thereof.

In another embodiment of the liquid composition disclosed herein, the at least one pharmaceutically acceptable excipient comprises a vehicle comprising water, an alcohol, or a combination thereof.

Exemplary alcohols include, but are not limited to, a C2 to C8 mono- and poly-alcohol (e.g., ethanol, glycerine, propylene glycol, and sorbitol), a linear or branched C7 to C18 alcohols.

In another embodiment of the liquid composition disclosed herein, the at least one pharmaceutically acceptable excipient comprises water and an alcohol, where the alcohol ranges from about 10% (w/v) to about 30% (w/v), and all values in between, including 11% (w/v), 12% (w/v), 13% (w/v), 14% (w/v), 15% (w/v), 16% (w/v), 17% (w/v), 18% (w/v), 19% (w/v), 20% (w/v), 21% (w/v), 22% (w/v), 23% (w/v), 24% (w/v), 25% (w/v), 26% (w/v), 27% (w/v), 28% (w/v), and 29% (w/v).

In yet another embodiment, the at least one pharmaceutically acceptable excipient comprises a vehicle comprising water and glycerine, wherein the glycerine is present in an amount of about 10% (w/v) to about 30% (w/v).

In yet another embodiment, the at least one pharmaceutically acceptable excipient comprises a vehicle comprising water and glycerine, wherein the glycerine is present in an amount of about 20% (w/v).

Still another embodiment of the liquid composition disclosed herein, the at least one pharmaceutically acceptable excipient comprises a preservative selected from the group consisting of methylparaben, ethylparaben, propylparaben, butylparben, isobutylparaben, sodium benzoate, potassium sorbate, benzoic acid, sorbic acid, benzyl alcohol, boric acid, butylated hydroxy anisole, cetylpyridinium chloride, a combination thereof.

Still another embodiment of the liquid composition disclosed herein, the at least one pharmaceutically acceptable excipient comprises a preservative in an amount of about 1 mg/mL to about 4 mg/mL. In some embodiments of the liquid composition disclosed herein, the at least one pharmaceutically acceptable excipient comprises a preservative in an amount of about 1 mg/mL, about 1.1 mg/mL, about 1.2 mg/mL, about 1.3 mg/mL, about 1.4 mg/mL, about 1.5 mg/mL, about 1.6 mg/mL, about 1.7 mg/mL, about 1.8 mg/mL, about 1.9 mg/mL, about 2.0 mg/mL, about 2.1 mg/mL, about 2.2 mg/mL, about 2.3 mg/mL, about 2.4 mg/mL, about 2.6 mg/mL, about 2.7 mg/mL, about 2.8 mg/mL, about 2.9 mg/mL, about 3.0 mg/mL, about 3.1 mg/mL, about 3.2 mg/mL, about 3.3 mg/mL, about 3.4 mg/mL, about 3.5 mg/mL, about 3.6 mg/mL, about 3.7 mg/mL, about 3.8 mg/mL, about 3.9 mg/mL or about 4.0 mg/mL.

In another embodiment of the liquid composition disclosed herein, the at least one pharmaceutically acceptable excipient comprises a sweetener selected from the group consisting of sucralose, maltilol, liquid glucose, monoammonium glycyrrhizinate, saccharin sodium, xylitol, sorbitan monoleate, sorbitol, sucrose, aspartame, acesulfame potassium, or a combination thereof.

Still another embodiment of the liquid composition disclosed herein, the at least one pharmaceutically acceptable excipient comprises a sweetener in an amount of about 0.1 mg/mL to 1.0 mg/mL.

In some embodiment of the liquid composition disclosed herein, the at least one pharmaceutically acceptable excipient comprises a sweetener in an amount of about 0.1 mg/mL, about 0.15 mg/mL, about 0.2 mg/mL, about 0.25 mg/mL, about 0.3 mg/mL, about 0.35 mg/mL, about 0.4 mg/mL, about 0.45 mg/mL, about 0.5 mg/mL, about 0.55 mg/mL, about 0.6 mg/mL, about 0.65 mg/mL, about 0.7 mg/mL, about 0.75 mg/mL, about 0.8 mg/mL, about 0.85 mg/mL, about 0.9 mg/mL, about 0.95 mg/mL, or about 1.0 mg/mL.

Still another embodiment of the liquid formulation disclosed herein exhibits an unexpected stability at a pH from about 4.5 to about pH 6.5.

In some embodiments the present formulation is stable at pH about 4.5, about 4.6, about 4.7, about 4.8, about 4.9, about 5.0, about 5.1, about 5.2, about 5.3, about 5.4, about 5.5, about 5.5, about 5.6, about 5.7, about 5.8, about 5.9, about 6.0, about 6.1, about 6.2, about 6.3, about 6.4 or about 6.5.

For instance, the composition disclosed herein having a pH range of from about 4.5 to about pH 6.5 exhibits a terazosin content of 100±10% labelled content for about 6-months, about 12 months, or about 24 months when stored at 25±2° C. and 60±5% relative humidity.

Alternatively, the composition disclosed herein having a pH range of from about 4.5 to about pH 6.5 exhibits a terazosin content of 100±5% labelled content for about 6-months, about 12-months, or about 24-months when stored at 25±2° C. and 60±5% relative humidity.

Further, the composition disclosed herein having a pH range of from about 4.5 to about pH 6.5 exhibits any individual specified impurity content (based on the content of terazosin) of not more than 0.4%, a prazosin impurity content of not more than 0.2%, any individual unspecified impurity content of not more than 0.2% and a total impurity of not more than 1.2% w/w for at least about 6-months when stored at 25±2° C. and 60±5% relative humidity.

Unless stated otherwise, the bottles used for the compositions described herein preferably comprise a white high density polyethylene (HDPE) bottles. The HDPE bottles described herein have volumes of 2.03 oz (60 mL). In a particular embodiment, the HDPE bottle is enclosed using a child resistant closure and bottles were sealed.

Still another embodiment of the liquid composition disclosed herein relates to the treatment of symptomatic benign prostatic hyperplasia (BPH) and hypertension. One may consult published prescribing information (e.g., HYTRIN® (terazosin hydrochloride) tablet prescribing information) for further details on dosing regimens and a therapeutically effective amount of terazosin as applicable to the treatment of symptomatic BPH and hypertension.

Still another embodiment of the liquid composition disclosed herein is free from one or more of the following ingredients such as sugar (e.g., sucrose), lactose, an antioxidant, and ethanol. The most hypertensive patient is diabetic especially geriatric patients; hence the sugar free formulation of the present invention is more beneficial for this patient group.

An antioxidant excluded from the liquid composition disclosed herein includes, for example, alpha tocopherol, ascorbic acid, ascorbyl palmitate, butylated hydroxyanisole, butylated hydroxytoluene, erythorbic acid, ethyl oleate, and sodium ascorbate.

Accordingly, one aspect relates to a method of treating symptomatic benign prostatic hyperplasia (BPH) and hypertension comprising administering to a patient in need thereof a therapeutically effective amount of a liquid composition disclosed herein. Another aspect relates to a method of treating hypertension comprising administering to a patient in need thereof a therapeutically effective amount of a liquid composition disclosed herein.

EXAMPLES

The following exemplified embodiments illustrate aspects of the liquid composition disclosed herein and should not be considered to be limiting on the claimed subject matter.

Examples 1 and 2

Table 1 includes the compositional makeup of Examples 1 and 2. A 1 Litre batch was manufactured as follows, Methylparaben was dissolved in purified water by heating at 80° C. followed by sodium benzoate was added to dissolve and allowed the solution to get into room temperature. To the above solution glycerine was added under stirring. To the above solution terazosin hydrochloride was added stirred to get clear solution. To the solution sucralose was added and stirred. The solution pH was adjusted to 4.50 (Example. 1) and 5.50 (Example. 2) using citric acid and sodium citrate dihydrate. Total volume of solution was adjusted with purified water to obtain oral liquid composition. A prepared 1.7 oz (50 mL) liquid pharmaceutical composition were dispensed to a 2.03 oz of White high density polyethylene bottles with 33 mm child resistant closure and stored inverted under various stability conditions, as outlined in Table 5.

TABLE 1

| | Example No. | | | |
|---|---|---|---|---|
| | Example. 1 | | Example. 2 | |
| Ingredients | mg/mL | % w/v | mg/mL | % w/v |
| Purified water | 600.00 | 60.00 | 600.00 | 60.00 |
| Methylparaben | 1.00 | 0.10 | 1.00 | 0.10 |
| Sodium benzoate | 1.00 | 0.10 | 1.00 | 0.10 |
| Glycerin | 200.00 | 20.00 | 200.00 | 20.00 |
| Terazosin Hydrochloride | 1.19 | 0.12 | 1.19 | 0.12 |
| Sucralose | 0.50 | 0.05 | 0.50 | 0.05 |
| Citric acid anhydrous | 0.70 | 0.07 | 0.10 | 0.07 |
| Sodium citrate dihydrate | 0.50 | 0.05 | 0.30 | 0.03 |
| Purified water | qs to mL | ~20.00 | qs to mL | ~20.00 |
| pH | 4.50 | | 5.50 | |
| Solution description | Clear colorless solution | | Clear colorless solution | |

Example-3

Table 2 includes the compositional makeup of Example 3. A 1 Litre batch was manufactured as follows, Methylparaben was dissolved in purified water by heating at 80° C. followed by sodium benzoate was added to dissolve and allowed the solution to get into room temperature. To the above solution glycerine was added under stirring. To the above solution terazosin hydrochloride was added stirred to get clear solution. To the solution sucralose was added and stirred. To the solution citric acid followed by sodium citrate dihydrate is dissolved under stirring. The required pH 6.5 was adjusted with 0.1N sodium hydroxide and stirred to obtain clear solution. Total volume of solution was adjusted with purified water to obtain oral liquid composition of terazosin. A prepared 1.7 oz (50 mL) liquid pharmaceutical composition were dispensed to a 2.03 oz of White high density polyethylene bottles with 33 mm child resistant closure and stored inverted under various stability conditions, as outlined in Table 5.

TABLE 2

| | Example No. Example. 3 | |
|---|---|---|
| Ingredients | mg/mL | % w/v |
| Purified water | 600.00 | 60.00 |
| Methylparaben | 1.00 | 0.10 |
| Sodium benzoate | 1.00 | 0.10 |
| Glycerin | 200.00 | 20.00 |
| Terazosin Hydrochloride | 1.19 | 0.12 |
| Sucralose | 0.50 | 0.05 |
| Citric acid anhydrous | 0.10 | 0.01 |
| Sodium citrate dihydrate | 0.30 | 0.03 |
| 0.1N NaOH | qs to pH | |
| Purified water | qs to mL | ~20.00 |
| pH | 6.50 | |
| Solution description | Clear colorless solution | |

Example-4

Table 3 includes the compositional makeup of Example 4. A 1 Litre batch was manufactured as follows, Methylparaben was dissolved in purified water by heating at 80° C. followed by sodium benzoate was added to dissolve and allowed the solution to get into room temperature. To the above solution glycerine was added under stirring. To the above solution terazosin hydrochloride was added stirred to obtain clear solution. To the solution sucralose was added and stirred. To the solution citric acid followed by sodium citrate dihydrate was added under stirring to obtain clear solution. Total volume of solution was adjusted with purified water to obtain final oral liquid composition of terazosin. A prepared 1.7 oz (50 mL) liquid pharmaceutical composition were dispensed to a 2.0 oz of White high density polyethylene bottles with 33 mm child resistant closure and stored inverted under various stability conditions.

TABLE 3

| Ingredients | Example No. Example 4 | |
|---|---|---|
| | mg/mL | % w/v |
| Purified water | 600.00 | 60.00 |
| Methylparaben | 2.00 | 0.20 |
| Propylparaben | 0.20 | 0.02 |
| Glycerin | 200.00 | 20.00 |
| Terazosin Hydrochloride | 1.19 | 0.12 |
| Sucralose | 0.50 | 0.05 |
| Citric acid anhydrous | 0.09 | 0.09 |
| Sodium citrate dihydrate | 0.30 | 0.03 |
| Purified water | qs to mL | ~20.00 |
| pH | 5.50 | |
| Solution description | Clear colorless solution | |

Examples 5 and 6

Table 4 includes the compositional makeup of Examples 5 and 6. A 1 Litre batch was manufactured as follows; Methylparaben was dissolved in purified water by heating at 80° C. and allowed the solution to get into room temperature. To the above solution glycerine was added under stirring. To the above solution terazosin hydrochloride was added with stirring to obtain clear solution. To the solution, sucralose was added and stirred. The solution pH was adjusted from 5.00 (Example. 5) to 6.00 (Example. 6) using citric acid and sodium citrate dihydrate. Total volume of solution was adjusted with purified water to obtain liquid composition. A prepared 1.7 oz (50 mL) liquid pharmaceutical composition were dispensed to a 2.03 oz of White high density polyethylene bottles with 33 mm child resistant closure and stored inverted under various stability conditions, as outlined in Table 5.

TABLE 4

| | Example No. | | | |
|---|---|---|---|---|
| | Example. 5 | | Example. 6 | |
| Ingredients | mg/mL | % w/v | mg/mL | % w/v |
| Purified water | 600.00 | 60.00 | 600.00 | 60.00 |
| Methylparaben | 2.00 | 0.20 | 2.00 | 0.20 |
| Glycerin | 200.00 | 20.00 | 200.00 | 20.00 |
| Terazosin Hydrochloride | 1.19 | 0.12 | 1.19 | 0.12 |
| Sucralose | 0.50 | 0.05 | 0.50 | 0.05 |
| Citric acid anhydrous | 0.075 | 0.007 | 0.075 | 0.007 |
| Sodium citrate dihydrate | 0.075 | 0.007 | 0.550 | 0.06 |
| Purified water | qs to mL | ~20.00 | qs to mL | ~20.00 |
| pH | 5.00 | | 6.00 | |
| Solution description | Clear colorless solution | | Clear colorless solution | |

Exemplified liquid compositions were stored inverted under different storage conditions 2-8° C., 25±5° C./60% relative humidity (RH) (viz., room temperature conditions), 40±2° C. 75% RH (viz., accelerated conditions).

Stored samples were analyzed for appearance and pH. The pH-values were measured in a manner consistent with USP <791>.

Stored samples also were analyzed for terazosin assay (% w/w). The reported amount of terazosin (expressed as Assay (% w/w) was determined by HPLC with reference to a suitable calibration curve using terazosin hydrochloride USP as reference standard.

Further, stored samples were analyzed for impurities and related substances (% w/w), such as Terazosin Related Compound A ("TZN RC A," CAS No. 60548-08-5, a hydrolysed degradation impurity), Prazosin ("PZN," CAS No. 19216-56-9), Terazosin Related Compound C ("TZN RC C," CAS No. 1486464-41-8), Doxazosin Related Compound C ("DZN RC C," CAS No. 23680-84-4, i.e., 2-Chloro-6,7-dimethoxy-4-quinazolinamine), Highest Unknown Impurities ("HUI"), and Total Impurities ("TI"). Amounts of impurities and related substances were determined by HPLC, as described in, for example, USP 29/NF 24 Terazosin Hydrochloride Monograph.

TABLE 5

Stability summary of selected exemplified embodiments controlled room temperature condition

| Example No. | Stability condition | pH | Assay (% w/w) | Related substances (% w/w) | | | | | |
|---|---|---|---|---|---|---|---|---|---|
| | | | | TZN RC A | PZN | TZN RC C | DZN RC C | HUI | TI |
| | Specification | | 90.0 to 110.0 | NMT 0.4 | NMT 0.2 | NMT 0.4 | NMT 0.4 | NMT 0.2 | NMT 1.2 |
| 1 | Initial | 4.49 | 101.4 | 0.156 | 0.012 | ND | 0.003 | 0.037 | 0.250 |
| | 25° C./60% RH-6M | 4.44 | 100.6 | 0.159 | ND | ND | ND | 0.042 | 0.287 |
| 2 | Initial | 5.51 | 100.8 | 0.054 | 0.012 | ND | 0.003 | 0.037 | 0.145 |
| | 25° C./60% RH-6M | 5.41 | 100.0 | 0.047 | 0.012 | ND | ND | 0.043 | 0.204 |

TABLE 5-continued

Stability summary of selected exemplified embodiments controlled room temperature condition

| | | | | Related substances (% w/w) | | | | | |
|---|---|---|---|---|---|---|---|---|---|
| Example No. | Stability condition | pH | Assay (% w/w) | TZN RC A | PZN | TZN RC C | DZN RC C | HUI | TI |
| 3 | Initial | 6.50 | 100.6 | 0.105 | 0.014 | ND | 0.003 | 0.036 | 0.205 |
| | 25° C./60% RH-6M | 6.41 | 99.4 | 0.109 | 0.011 | ND | ND | 0.036 | 0.265 |

Abbreviations: TZN RC A (Terazosin Related Compound A), PZN (Prazosin), TZN RC C (Terazosin Related Compound C), DZN RC C (Doxazosin Related Compound C), HUI (Highest Unknown Impurities), TI (Total Impurities), M (month), and RH (relative humidity).

The above table shows that exemplified liquid compositions described herein are suitable for pharmaceutical use insofar that samples stored under room temperature conditions (25° C./60% RH) exhibit a terazosin assay of 100±10% for at least 6 months as well as an amount of Terazosin Related Compound A of not more than 0.4%.

Additional data shows that a reduction in pH i.e pH of 3.5 results in an increased amount of degradation, as evidenced by the formation of Terazosin Related Compound A.

TABLE 6

Assay & Impurity profile of pH 3.5 exemplified embodiment under controlled room temperature condition

| | | | | Related substances (% w/w) | | | | | |
|---|---|---|---|---|---|---|---|---|---|
| Stage | pH | Assay (% w/w) | TZN RC A | PZN | TZN RC C | DZN RC C | HUI | TI | |
| Specification | | 90.0 to 110.0 | NMT 0.4 | NMT 0.2 | NMT 0.4 | NMT 0.4 | NMT 0.2 | NMT 1.2 | |
| Initial | 3.51 | 105.4 | 0.644 | 0.014 | ND | ND | 0.038 | 0.732 | |

Abbreviations: TZN RC A (Terazosin Related Compound A), PZN (Prazosin), TZN RC C (Terazosin Related Compound C), DZN RC C (Doxazosin Related Compound C), HUI (Highest Unknown Impurities), TI (Total Impurities), M (month), and RH (relative humidity).

The subject matter of Indian Patent Application No. 202041035308, filed on Aug. 17, 2020, is incorporated by reference in its entirety. Additionally, the subject matter of the documents cited herein is incorporated by reference in their entirety to the extent necessary. In the event that there is a difference in meaning between the incorporated terms and the terms disclosed herein, the meaning of the terms disclosed herein will control.

Those skilled in the art will also appreciate that various adaptations and modifications of the preferred and alternative embodiments described above can be configured without departing from the scope and spirit of the disclosure. Therefore, it is to be understood that, within the scope of the appended claims, the disclosure may be practiced other than as specifically described herein.

We claim:

1. A liquid composition for oral administration, comprising:
   i. terazosin or a pharmaceutically acceptable salt thereof in an amount of about 1 to about 5 mg/mL;
   ii. about 0.15 mg/mL to about 2 mg/mL of at least one pH modifier;
   iii. at least one pharmaceutically acceptable excipient, wherein the at least one pharmaceutically acceptable excipient comprises a preservative in an amount of about 2 mg/mL to about 4 mg/mL and selected from the group consisting of methylparaben, propylparaben, ethylparaben, butylparaben, isobutylparaben, sodium benzoate, potassium sorbate, benzoic acid, sorbic acid, benzyl alcohol, boric acid, butylated hydroxy anisole, cetylpyridinium chloride, and a combination thereof, and
   iv. a vehicle comprising water and glycerine; said glycerine is present in an amount of about 20% w/v;

wherein the oral liquid composition has a pH of about 4.5 to about 6.5.

2. The liquid composition of claim 1, comprising terazosin hydrochloride.

3. The liquid composition of claim 1, wherein the amount of terazosin ranges from about 1 mg/mL to about 4 mg/mL.

4. The liquid composition of claim 1 comprising about 1 mg/mL of terazosin.

5. The liquid composition of claim 1, wherein the at least one pH modifier is selected from the group consisting of citric acid, malic acid, hydrochloric acid, phosphoric acid, ammonium chloride, potassium bicarbonate, potassium carbonate, sodium acetate, sodium chloride, a trisodium citrate salt, sodium hydroxide, sodium phosphate, sodium thiosulfate, tartaric acid, calcium chloride, sodium bisulphate, fumaric acid, sodium dihydrogen phosphate monohydrate, disodium hydrogen phosphate dihydrate, potassium phosphate, and a combination thereof.

6. The liquid composition of claim 1, wherein the amount of the at least one pH modifier ranges from about 0.15 mg/mL to about 0.7 mg/mL.

7. The liquid composition of claim 1, wherein the at least one pharmaceutically acceptable excipient further comprises a sweetener.

8. The liquid composition of claim 1, wherein the at least one pharmaceutically acceptable excipient further comprises an alcohol.

9. The liquid composition of claim 1, wherein the at least one pharmaceutically acceptable excipient further comprises a C2 to C8 mono- and poly-alcohol, a linear or branched C7 to C18 alcohol, and a combination thereof.

10. The liquid composition of claim 1, wherein the at least one pharmaceutically acceptable excipient does not further include sugar, lactose, an antioxidant, and ethanol.

11. The liquid composition of claim 1, wherein the preservative is selected from the group consisting of methylparaben, propylparaben, sodium benzoate, potassium sorbate, benzoic acid, sorbic acid, and a combination thereof.

12. The liquid composition of claim 1, wherein the at least one pharmaceutically acceptable excipient further comprises a sweetener selected from the group consisting of sucralose, maltilol, liquid glucose, monoammonium glycyrrhizinate, saccharin sodium, xylitol, sorbitan monoleate, sorbitol, sucrose, aspartame, acesulfame potassium, and a combination thereof.

13. The liquid composition of claim 1, wherein the preservative is present in an amount of about 2 mg/mL to about 3 mg/mL.

14. The liquid composition of claim 1, wherein the at least one pharmaceutically acceptable excipient further comprises a sweetener in an amount of about 0.1 mg/mL to about 1.0 mg/mL.

15. The liquid composition of claim 1 having a pH of about 5.0 to about 6.0.

16. The liquid composition of claim 1, wherein the composition exhibits a terazosin content of 100±10% labelled content for about 6-months when stored at 25±2° C. and 60±5% relative humidity.

17. A method of treating symptomatic benign prostatic hyperplasia (BPH) comprising administering to a patient in need thereof a therapeutically effective amount of the liquid composition of claim 1.

18. A method of treating hypertension comprising administering to a patient in need thereof a therapeutically effective amount of the liquid composition of claim 1.

19. The liquid composition of claim 1, wherein the at least one pH modifier is selected from the group consisting of citric acid, a disodium citrate salt, a trisodium citrate salt, phosphoric acid, sodium phosphate, sodium dihydrogen phosphate monohydrate, disodium hydrogen phosphate dihydrate, potassium phosphate, and a combination thereof.

20. The liquid composition of claim 19, wherein the amount of the at least one pH modifier ranges from about 0.15 mg/mL to about 0.7 mg/mL.

* * * * *